United States Patent
Zhang

(10) Patent No.: US 10,272,455 B2
(45) Date of Patent: Apr. 30, 2019

(54) PORTABLE PNEUMATIC ATOMIZING DEVICE

(71) Applicant: Chongshi Zhang, Guizhou (CN)

(72) Inventor: Chongshi Zhang, Guizhou (CN)

( * ) Notice: Subject to any disclaimer, the term of this patent is extended or adjusted under 35 U.S.C. 154(b) by 0 days.

(21) Appl. No.: 15/656,118

(22) Filed: Jul. 21, 2017

(65) Prior Publication Data

US 2019/0022677 A1 Jan. 24, 2019

(51) Int. Cl.
*B05B 17/06* (2006.01)
*B05B 7/00* (2006.01)
*B05B 12/02* (2006.01)
*A61M 15/00* (2006.01)
*A61M 11/00* (2006.01)
*B05B 15/62* (2018.01)

(52) U.S. Cl.
CPC ......... *B05B 7/0081* (2013.01); *A61M 11/005* (2013.01); *A61M 15/009* (2013.01); *B05B 12/02* (2013.01); *B05B 15/62* (2018.02); *B05B 17/06* (2013.01); *A61M 2205/8206* (2013.01); *A61M 2209/088* (2013.01)

(58) Field of Classification Search
CPC ....... B05B 7/0081; B05B 15/62; B05B 12/02; B05B 17/06; A61M 11/005; A61M 15/009
USPC ......... 239/102.1, 102.2, 128, 152, 153, 289, 239/290, 302, 340, 369, 409, 332
See application file for complete search history.

(56) References Cited

U.S. PATENT DOCUMENTS

| | | | | |
|---|---|---|---|---|
| 5,837,167 | A * | 11/1998 | Lederer | B01F 3/04035 261/28 |
| 6,216,961 | B1 * | 4/2001 | Utter | B05B 7/0075 239/289 |
| 6,378,845 | B1 * | 4/2002 | Hsu | F24F 6/00 239/289 |
| 2007/0257383 | A1 * | 11/2007 | Chan | F24F 6/04 261/107 |
| 2009/0143004 | A1 * | 6/2009 | Tam | F24F 5/0035 239/289 |

\* cited by examiner

*Primary Examiner* — Steven J Ganey
(74) *Attorney, Agent, or Firm* — Wayne & Ken, LLC; Tony Hom

(57) ABSTRACT

The present invention provides a potable pneumatic atomizing device. It includes a mounting seat, a small type fan, a water tank, an ultrasonic atomizing piece and a fixing clip. The small type fan and the water tank are respectively installed on the upper part and the side part of the mounting seat, and an air passage is formed among the small type fan, the water tank and the mounting seat; the mounting seat is provided with a lifting support frame, the lifting support frame stretches the clothes to extend the gap between the clothes and the human body. The ultrasonic atomizing piece is arranged on the top of the water tank and atomizes water in the water tank to release into the gap between clothes and the human body. The small type fan transfers outside air into the air passage, then passing the air passage, into the gap.

10 Claims, 9 Drawing Sheets

# PORTABLE PNEUMATIC ATOMIZING DEVICE

FIELD OF THE INVENTION

The present invention relates to atomizing device technology field, more particularly relates to a potable pneumatic atomizing device.

BACKGROUND OF THE INVENTION

As the rapid development of the heavy industry and the increasing population result that the demand for the thermal power generation have increased. And both the emission of automobile exhaust and the amount of out-door air-conditioner soar. All of these cause the climate warming.

In order to alleviate the discomfort caused by climate warming, air-conditioner and AC motor fan become the necessities of life. Recently many kinds of cooling garment products using different working principle to reduce body surface temperature are appeared in market. The general pattern of the most popular cooling garment is zipper jacket with opening and closing fore breast. The basic technology of the cooling garment is that in use all of the other part of the cooling garment is close except cuffs and neckline. When the power is connected, two small-sized DC fan installed at the circular opening at the left and right ends of the waist in the cooling garment blows in the clothes. The principle is that when the body surface is completely wet by sweat, the fan installed on the clothes transfers air lower than the body surface temperature from outside the clothes into it, and form circulating airflow in the space between the body and the clothes. When the airflow glide along the body surface, it rapidly evaporates the sweat attached to the body surface to produce heat of vaporization effect, therefor reducing the temperature of the body surface. At the same time, the heat in the blood that is contained in the capillaries of the body is expelled from body as the sweat evaporates. This phenomenon is transmitted to the human brain through the epidermal nerve, so the human body feels cool. This series of physiological process constitute so-called physiological effect of human body air conditioning.

However, for the human body, water in the human body is, after all, a valuable and indispensable resource. When the amount of sweat secreted to a certain extent, in order to maintain that the function of other organs of the body will not cause dysfunction because of lack of water, or the body will not cause dehydration symptoms because of the large loss of water, the body will slow down the speed of the secretion of sweat, and less sweat is secreted from the sweat glands. What happens is that very limited sweat is secreted and evaporates instantaneously. So the cool effect at initially using cooling garment will be more and more not obvious. In addition, if the outside temperature of the cooling garment is close to the body temperature, or higher than the body temperature, then use the cooling garment, input equal to or higher than the body temperature of air into the cooling garment, the effect will be counterproductive things.

This shows that the cooling garment can not be durable and effective to cool the human body in the hot conditions.

SUMMARY OF THE INVENTION

In order to overcome the defects of the prior art, the present invention provides a potable pneumatic atomizing device. When the human body is in the dressed state, the water mist generator turns the water in the tank into water mist by means of atomization, the small-type fan transfers the air outside the clothes into the gap between the clothes and the human body, the water mist and the air mix and slide along the body surface with the flow to wet the skin surface, so as to reduce the temperature of the human body.

The technical proposals of the invention are as follows: a potable pneumatic atomizing device, include a mounting seat, a small-type fan, a water tank, a ultrasonic atomizing piece and a fixing clip. The small-type fan and the water tank are respectively installed on the upper part and the side part of the mounting seat, and an air passage is formed among the small type fan, the water tank and the mounting seat; the mounting seat is provided with a lifting support frame, the lifting support frame stretches the clothes to extend the gap between the clothes and the human body. The ultrasonic atomizing piece is arranged on the top of the water tank, and atomizes the water in the water tank to release into the gap between the clothes and the human body. The small type fan transfers the outside air into the air passage, then passing the air passage, into the gap between the clothes and the human body. The included angle between the directions that the air and the water mist enter into the gap between the clothes and the human body is beta anger, $0<\beta\leq45°$.

The mounting seat has a base, the two sides of the base are respectively extended out of one arm; the water tank is arranged at the upper end of the base and is positioned between the two arms.

The small type fan includes a shell, a fan assembly and a power assembly. The shell, the arms, the water tank and the base are combined to form the air passage. The shell has an air diversion portion and a fan portion. The air diversion portion is mounted on the arms and the base in a direction substantially parallel to the base and the water tank. The lower part of the air diversion portion protrudes downwards and outwards in a linear shape to form the fan portion. The included angle between the directions of the fan portion and the air diversion portion are set as alpha anger, $90<\alpha<180$, so as to the included angle between the direction of air entering the air passage and out flowing of the air passage is alpha angle. The fan assembly is accommodated in the fan portion.

The fan portion is provide with a safety net cover, the function of the safety net cover is to prevent user's fingers or strips of hard material inserted into the fan portion.

The support frame is provided with a support plate, both ends of the supporting plate respectively extends a connecting piece, the connecting piece extends downwards to form a elongated slider, the centre of the slider is hollowed out into a slide slot; on the upper part of both sides of the water tank is respectively provided with a limiting piece, the limiting piece passes through the slide slot to slide mount the support frame on the water tank, and limits the lifting distance of the sliding piece.

One side of the slider is attached to one side of the arm, the other side of the slider is a jagged edge; the two sides of the water tank is also respectively provided with an teeth block, wherein the teeth block is meshed with the jagged edge.

The clothes fixing clamp is arranged at the upper part of the small type fan; the clothes fixing clamp is an elastic piece in W shape, M shape, U shape, O shape, V shape, N shape or T shape.

The water tank comprises a box body, a box cover and a suction fiber mandrel tube; the box cover is buckled on the box body; an opening is arranged on the box cover, and water is poured into the box through the opening; the box cover is provided with an installation groove, the installation groove is provided with the ultrasonic atomizing piece; the suction fiber mandrel tube is aslant arranged in the box body; a suction fiber mandrel and a spring are arranged in the suction fiber mandrel tube, and the spring is arranged between the bottom end surface of the suction fiber mandrel and the sealing surface at the bottom of the suction fiber mandrel tube.

The side of the lower end of the suction fiber mandrel tube is provided with an inlet; the water in the water tank enters the suction fiber mandrel tube by the inlet to moist the suction fiber mandrel.

Both sides of the water tank are arranged a belt fixed buckle, the function of the belt fixed buckle is that when the clothes fixing clamp can not achieve the best fixed state, a ribbon is used to go through the fixed buckle and around the user's body to fix the potable pneumatic atomizing device.

The present invention has beneficial effects: as follows: the potable pneumatic atomizing device, when the human body is in the dressed state, the water mist generator turns the water in the tank into water mist by means of atomization, at the same time, the small-type fan transfers the air outside the clothes into the gap between the clothes and the human body, the water mist and the air mix and slide along the body surface with the flow to wet the skin surface, so as to reduce the temperature of the human body. The included angle between the directions that the air and the water mist enter into the gap between the clothes and the human body is among 0~45°, so that the airflow can disperse the mist, and slide along the body surface with the mist, so as to fully disperse mist, therefor that it can be distributed on the body surface.

DETAILED DESCRIPTION OF ILLUSTRATED EMBODIMENTS

Figure 1:
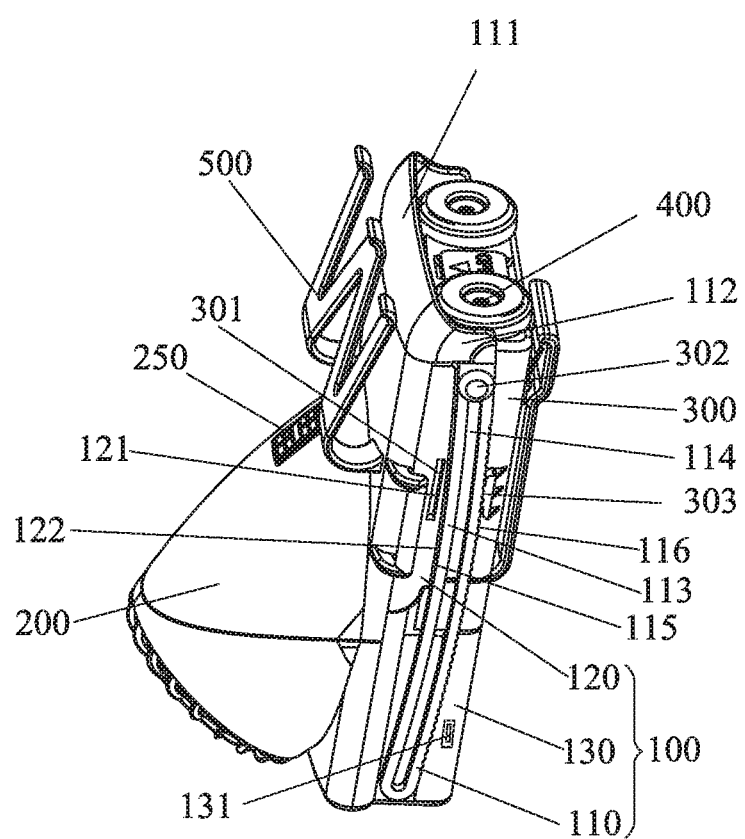
FIG. 1 is a schematic diagram of the portable pneumatic atomizing device of the present invention.
Figure 2:
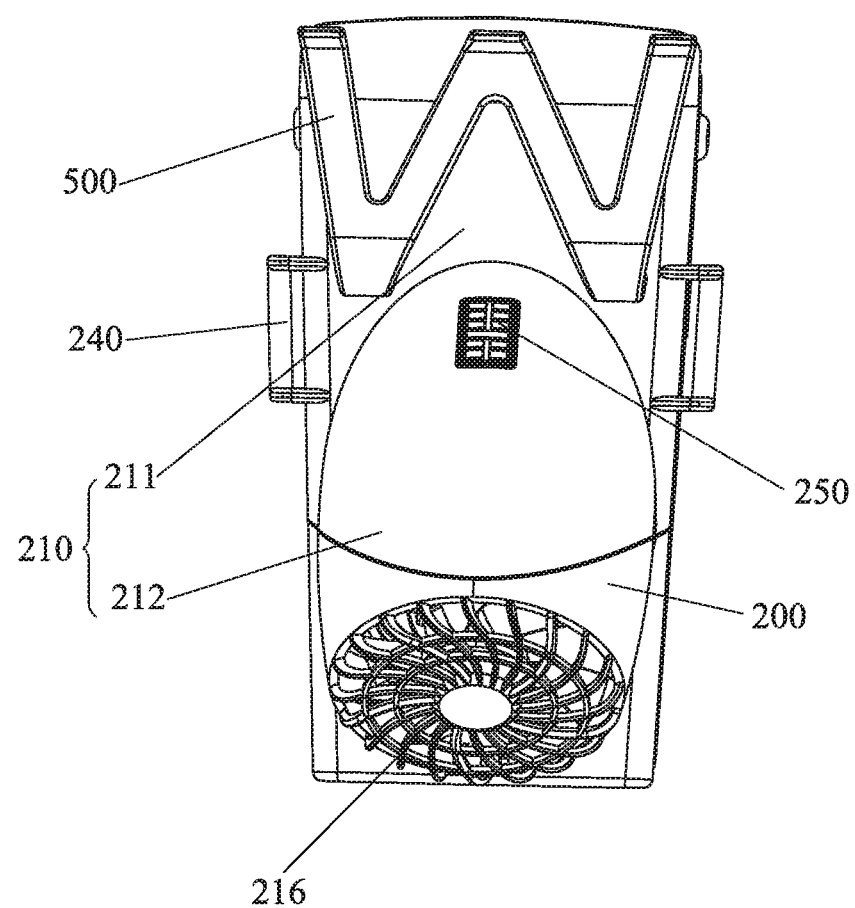
FIG. 2 is a schematic diagram of side structure of the portable pneumatic atomizing device of the present invention.
Figure 3:
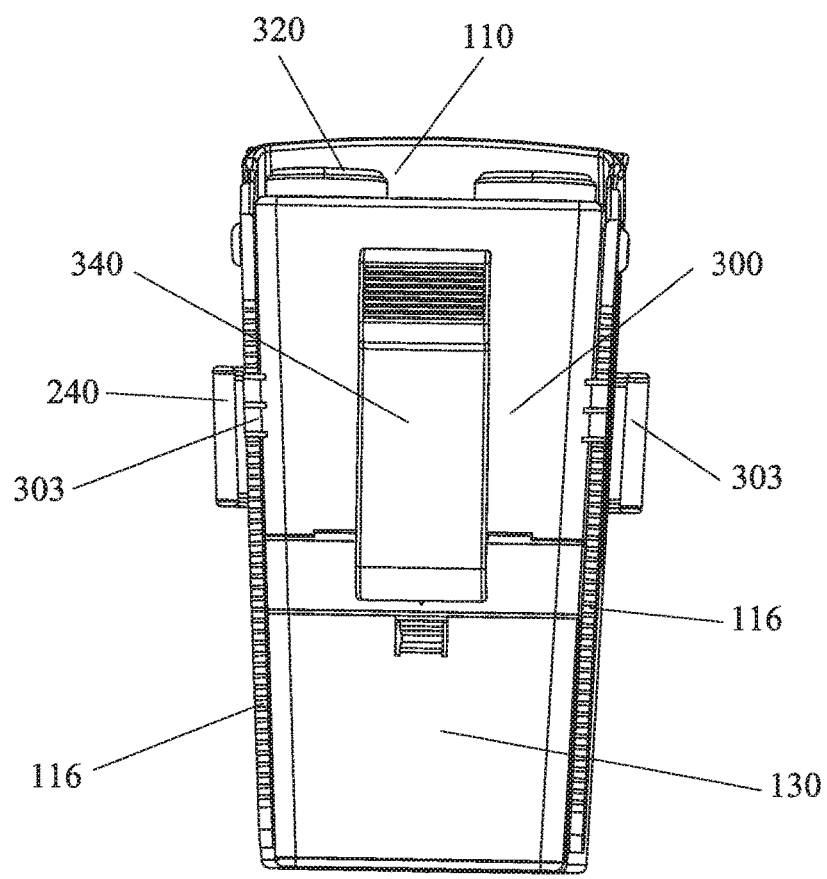
FIG. 3 is a schematic diagram of another side structure of the portable pneumatic atomizing device of the present invention.
Figure 4:
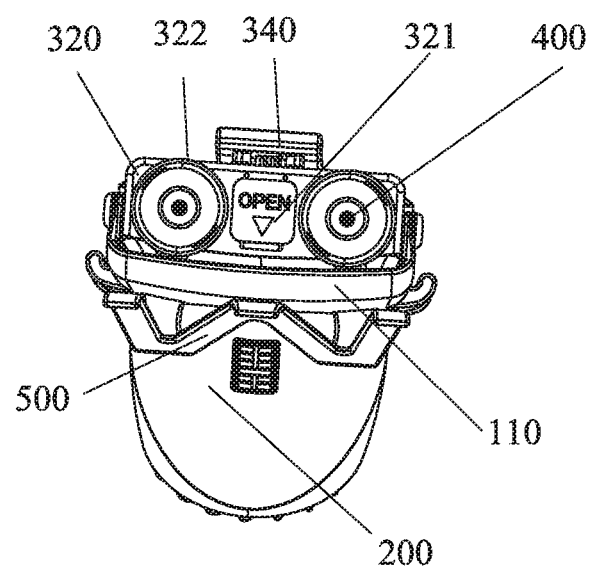
FIG. 4 is a top view of the portable pneumatic atomizing device of the present invention.
Figure 5:
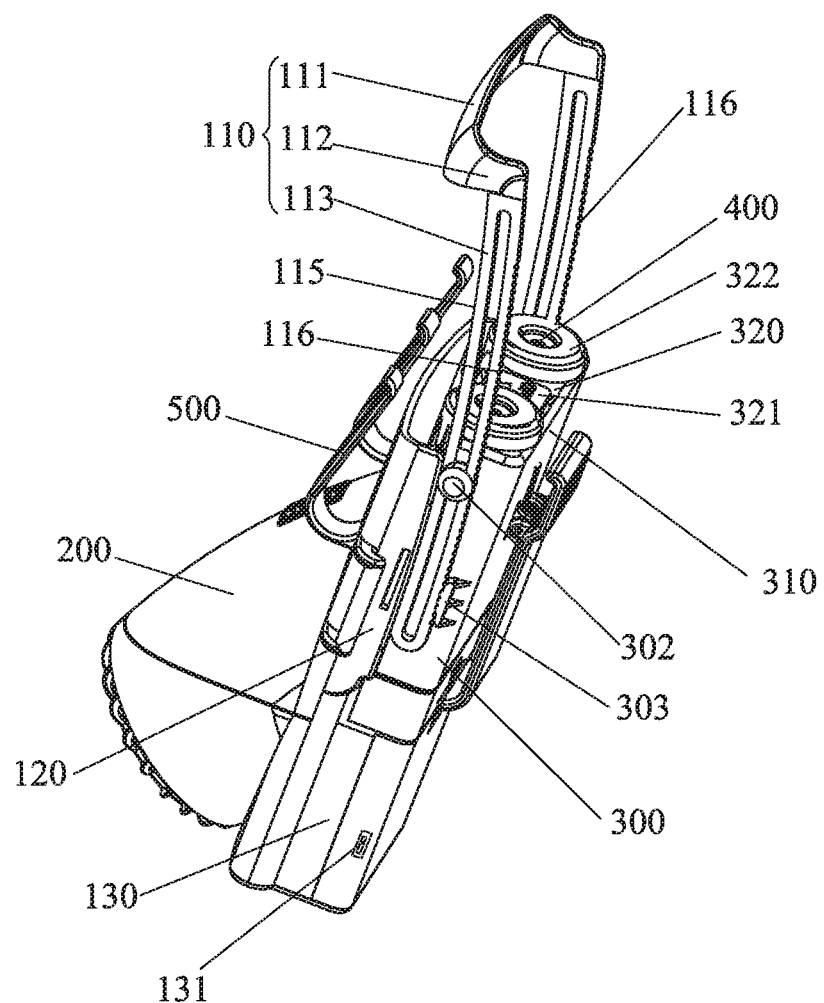
FIG. 5 is a schematic diagram in the use state of the portable pneumatic atomizing device according to the present invention.

In order to describe the object of the invention, technical scheme and technical effect more clear, the follow will combine the embodiment of the invention to further explain the present invention. It should be understood that the described embodiments are not only used to explain the present invention, not for defining the scope of the present invention.

Referring to FIG. 1, FIG. 2, FIG. 3, FIG. 4, FIG. 5, FIG. 6 and FIG. 7, a potable pneumatic atomizing device, include a mounting seat 100, a small-type fan 200, a water tank 300, a ultrasonic atomizing piece 400 and a fixing clip 500. The mounting seat 100 is provided with a lifting support frame 110, the lifting support frame 110 stretches the clothes to extend the gap between the clothes and the human body. The small-type fan 200 and the water tank 300 are respectively installed on the upper part and the side part of the mounting seat 100, and an air passage F is formed among the small type fan 200, the water tank 300 and the mounting seat 100. The ultrasonic atomizing piece 400 is arranged on the top of the water tank 300, and atomizes the water in the water tank 300 to release into the gap between the clothes and the human body. The small type fan 200 transfers the outside air into the air passage F, then passing the air passage, into the gap between the clothes and the human body, and the air mixes with the water mist. The included angle between the directions that the air and the water mist enter into the gap between the clothes and the human body is beta anger, $0<\beta\leq45°$. The potable pneumatic atomizing device, when the human body is in the dressed state, the ultrasonic atomizing piece 400 turns the water in the tank into water mist by means of an ultrasonic shock, at the same time, the small-type fan transfers the air outside the clothes into the gap between the clothes and the human body, the water mist and the air mix and slide along the body surface with the flow to wet the skin surface, so as to reduce the temperature of the human body. The included angle between the directions that the air and the water mist enter into the gap between the clothes and the human body is among 0~45°, so that the airflow can disperse the mist, and slide along the body surface with the mist, so as to fully disperse mist, therefor that it can be distributed on the body surface.

The mounting seat 100 has a base 130, the two sides of the base 130 are respectively extended out of one arm 120. The water tank 300 is arranged at the upper end of the base 130 and is positioned between the two arms 120. It shall be understood that the connecting way of the water tank 300 and the base 130 can be arranged as a fixed connection or a removable connection as needed. When it is fixed connection, the connection way can be integrally molded, riveting, welding or screw connection etc. When it is disassembled, the connection way can be connected by clamping. It shall be understood that, without departing from the basic conception of the present invention, the structure of the connection of the water tank 300 and the base 130 shall be deemed to be within the limits of the protection claimed by the present invention. Preferably, in one embodiment of the invention, the water tank 300 and the 120 arms are respectively arranged on the matching block 301 and slot 121, the block 301 is accommodated in the slot 121, so that a removable connection of the water tank 300 and the side arm 121 is achieved.

The support frame 100 is provided with a support plate 111, both ends of the supporting plate 111 respectively extends a connecting piece 112, the connecting piece 112 extends downwards to form a elongated slider 113, the centre of the slider 113 is hollowed out into a slide slot 114; on the upper part of both sides of the water tank 300 is respectively provided with a limiting piece 302, the limiting piece 302 passes through the slide slot 114 therefor slide mounting the support frame 110 on the water tank 300 and preventing the slider 113 from the water tank 300 off. One side 115 of the slider 113 is attached to one side 122 of the arm 120, the other side of the slider is a jagged edge 116; the two sides of the water tank are also respectively provided with an teeth block 303, the teeth block 303 is meshed with the jagged edge 116, thus when the sliding piece 113 lift to a certain position, it will not naturally fall under the influence of gravity.

The jagged edge 116 of the slider 113 is integrally arc-shaped, and the arc radian is close to the physiological curve of the ordinary human body, and the slider 113 does not touch the human skin when the supporting plate 111 stretches the clothes.

The small type fan 200 comprises a shell 200 a fan assembly 220 and a power assembly 230.

Figure 6:
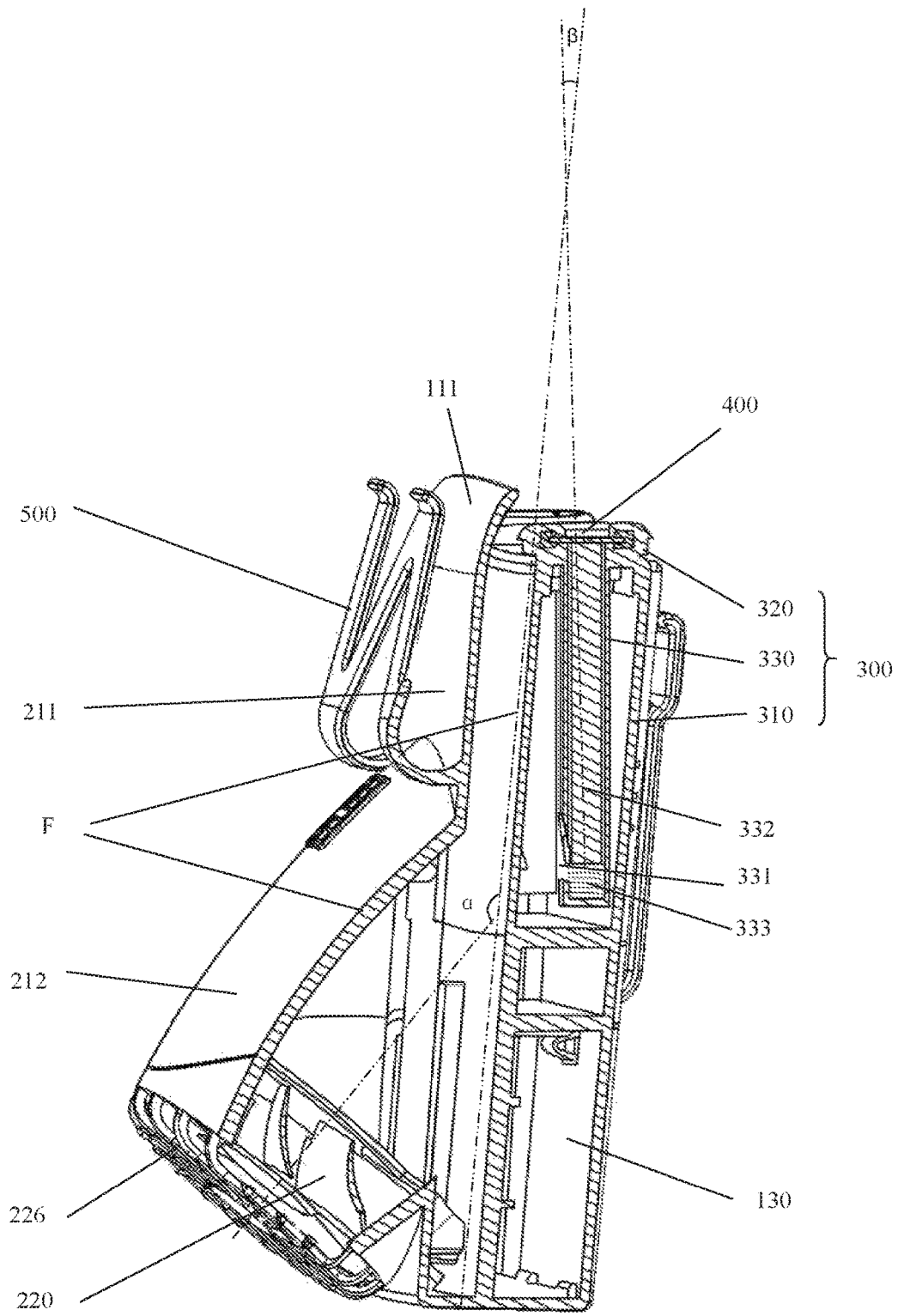
FIG. 6 is a cutaway view of the portable pneumatic atomizing device of the present invention.

Referring to FIG. 6, the shell 210, and the water tank 300, the arms 120 and the base 130 are combined to form the air passage F. The shell 210 has an air diversion portion 211 and a fan portion 212. The air diversion portion 211 is mounted on the arms 120 and the base 130 in a direction substantially parallel to the base 130 and the water tank 300. In order to prevent the airflow from colliding with the base 130 or the water tank 300 when it flows to the air channel F, as results that the wind pressure intensity to the air passage F is reduced. The lower part of the air diversion portion 211 protrudes downwards and outwards in a linear shape to form the fan portion 212. The included angle between the directions of the fan portion 212 and the air diversion portion 211 are set as alpha anger, $90<\alpha<180$, so as to the included angle between the direction of air entering the air passage and out flowing of the air passage is alpha angle. The fan portion 212 is provide with a safety net cover 216, the function of the safety net cover 216 is to prevent user's fingers or strips of hard material inserted into the fan portion.

Figure 7:
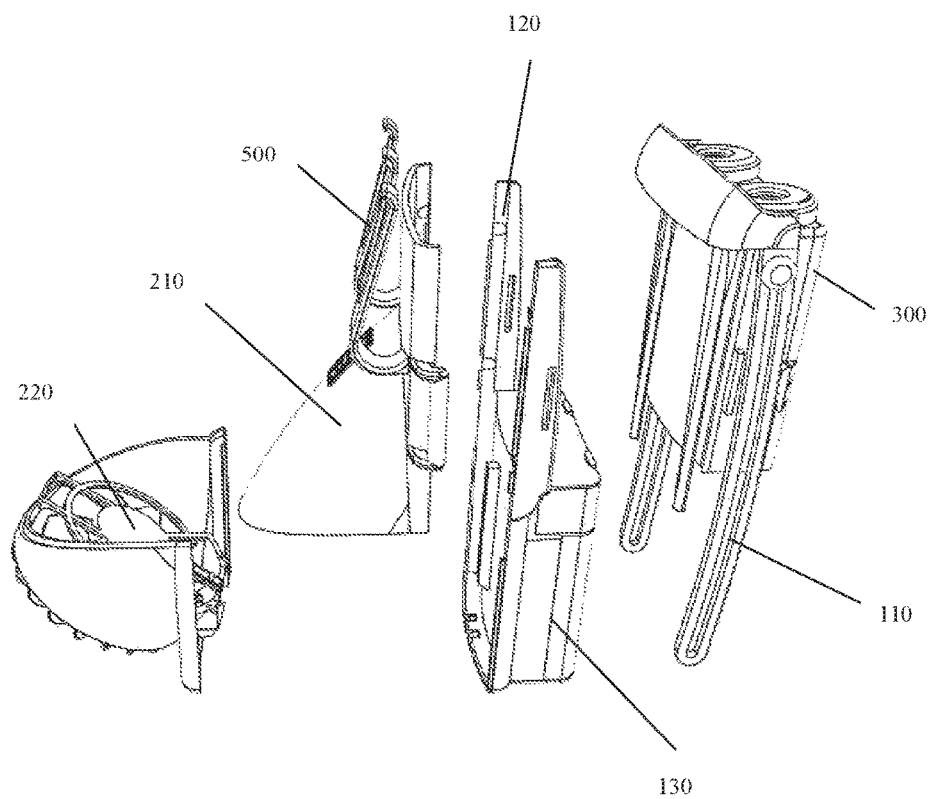
FIG. 7 is a decomposition schematic diagram of the portable pneumatic atomizing device according to the invention.

Referring to FIG. 7, for convenient to production, the shell 210 is cut into the upper part and lower part, the upper part and the lower part are respectively composed of a part of the air diversion portion 211 and a part of the fan portion 212.

Figure 8A:
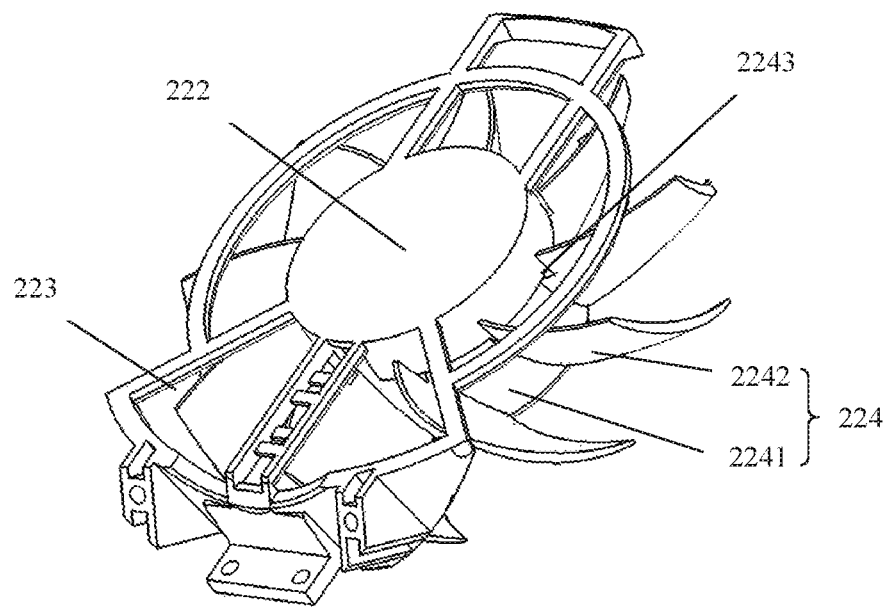
FIG. 8a is a schematic diagram of a fan assembly 220 of a portable pneumatic atomizing device according to the present invention.
Figure 8B:
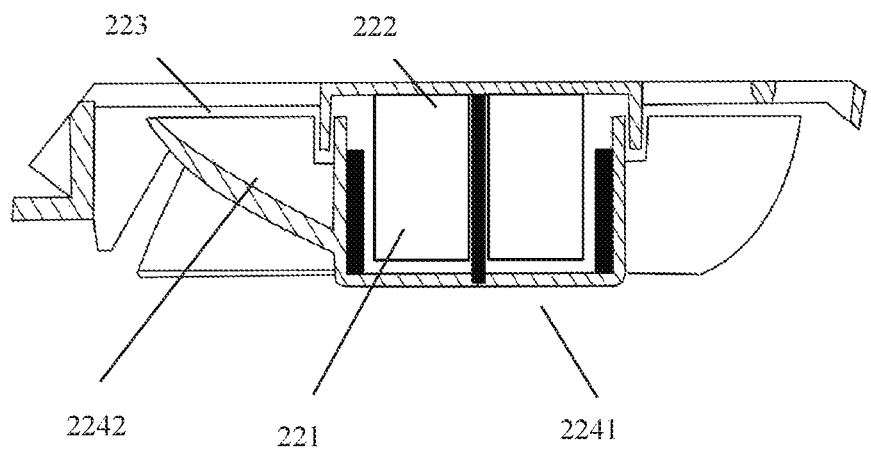
FIG. 8b is a cutaway view of a fan assembly 220 of the portable pneumatic atomizing device of the present invention.
Figure 9:
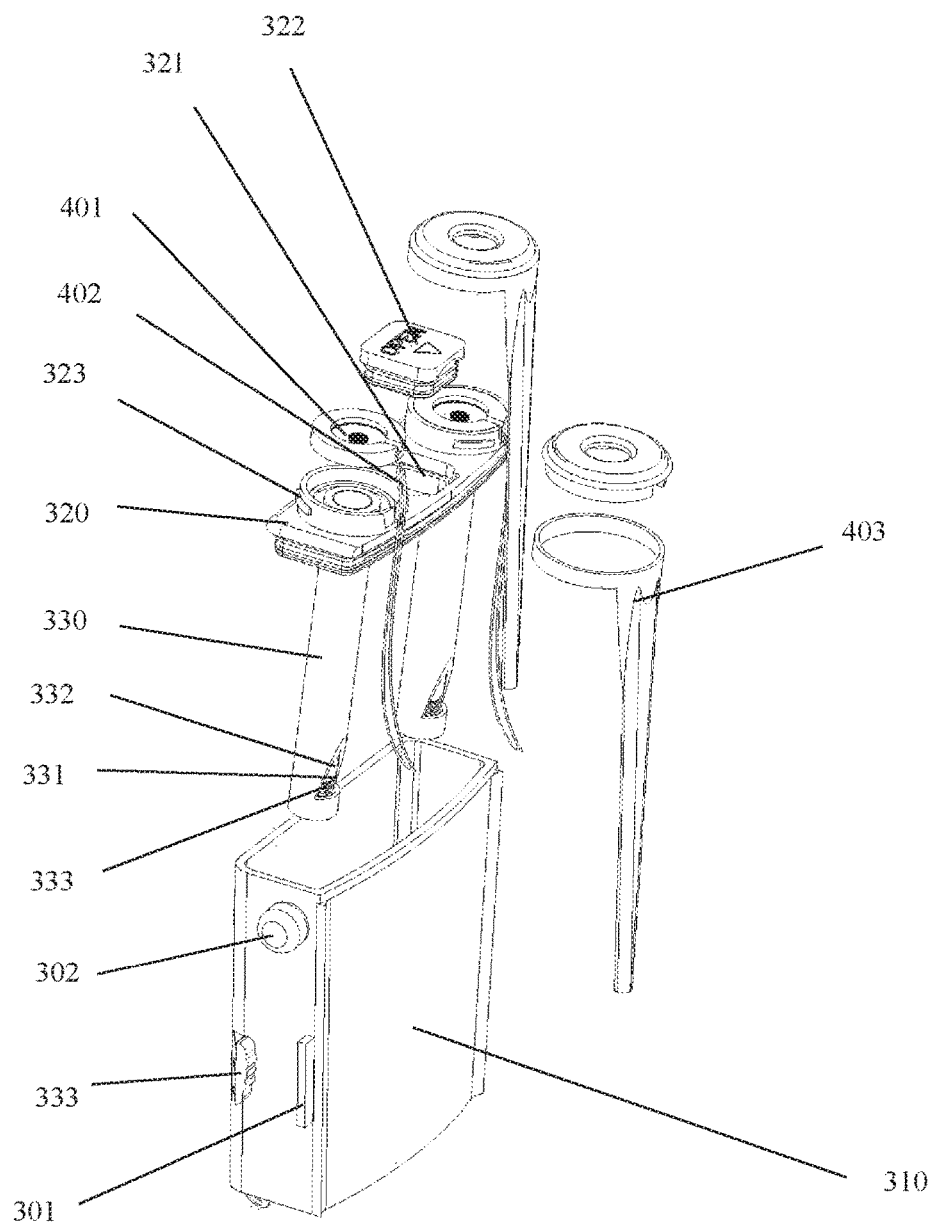
FIG. 9 is a decomposition schematic diagram of a water tank 300 of the portable pneumatic atomizing device of the present invention.

Referring to FIG. 8, The fan assembly 220 is accommodated in the fan portion 212. The main portion of the fan assembly 220 is accommodated in the fan portion at the lower part of the shell 210. The fan assembly 220 includes a fan motor 221, an electrical motor base 222, a connecting support 223 and an impeller 224. In order to prevent accidents, for example when add water to the tank water, or the ultrasonic atomizing piece is leakage, water passes the air channel F to fall in the fan assembly 220, causing a short circuit, the electrical part of the fan assembly 220 is set as closed nested in the motor base 222 and the impeller 224. Concretely, the side surface of the motor base 222 toward the safety net cover 216 is arranged as a groove. The impeller 224 has a motor shell 2241 and a blade 2242 set on the motor shell. The motor shell 2241 is nested within the motor base 222. The fan motor 221 is fixed in the motor base 222 and located in the motor shell 2241. The connection support 223 is provided on the motor base 222 to connect the motor base and the shell so as to achieve the installation of the fan assembly 220.

Preferably, in order to prevent the blade touching the motor base 222 to producing friction when the blade 2241 is rotating, the blade 2241 is provided with a L shaped incision 2243 in a corner close to the motor base 222.

The power assembly 230 is accommodated in the base 130. The power assembly 230 is electrically connected with the fan assembly 220. The fan assembly 220 absorbs the outside air through the safety net cover 216 into the fan portion 213, the airflow is stopped by the base 130, turning along the gap between the water tank 300 and the air diversion portion 211 out of the air passage F, and is sent to the gap between the clothes and the human body.

The top of the shell 210 and the bottom of the supporting plate 111 match each other in shape, the bottom of the support plate 111 to the top of the support plate 111 is curved transition gradually close to the box cover 320 at the top of the water tank 300, which guide the flow direction of the airflow, and cause more fully mixed the water mist and the flow, then flow along parallel to the body surface.

Preferably, the clothes fixing clip 500 is arranged in the shell 210. The clothes fixing clip 500 is shrapnel. Preferably, the shrapnel is in W shape, M shape, U shape, O shape, V shape, N shape or T shape etc. It shall be understood that the shape of the clothes fixing clip 500 can be arbitrarily varied as needed, for example, it can be set as the manufacturer's logo graphics or words etc. The shape of the clothes fixing clip 500 is not limited in the present invention. Without departing from the basic conception of the invention, any change in the shape of the clothes fixing clip 500 shall be deemed to be within the limits of the protection of the claims of this invention.

Refer to FIG. 1 and FIG. 9, the water tank 300 comprises a box body 310, a box cover 320 and a suction fiber mandrel tube 330, and the box cover 320 is buckled on the box body 310. The box cover 320 is connected with the box body 310 by a buckle type, so that the user can take down the box cover 320 and clean the inner part of the water tank 310. On the box cover 320 is provided with an opening 321 and an water cover 322 matched with the opening 321, and water is poured into the box through the opening. The box cover 320 is provided with an installation groove 323, the installation groove 323 contains the ultrasonic atomizing piece 400. The ultrasonic atomizing sheet 400 has the conventional structure, including an atomization thin 401 and pulse circuits 402 and card slots 403. The present invention does not go into details. The suction fiber mandrel tube 330 is aslant arranged in the box body 310. A water inlet 331 is arranged at the lower end of the suction fiber mandrel tube 330. The water in the box body enter into the suction fiber mandrel tube 330 by passing the water inlet 331. A suction fiber mandrel 332 and a spring 333 are arranged in the suction fiber mandrel tube 330, and the spring 333 is arranged between the bottom end surface of the suction fiber mandrel 332 and the sealing surface at the bottom of the suction fiber mandrel tube 330. Water in the water tank passes through the water inlet 331 into the suction fiber mandrel tube 330, and the part of the suction fiber mandrel 332 not immersing in water is also moisture. Because when the ultrasonic atomizing piece 400 is in working state, it has the characteristics of an ultrasonic micro vibration, therefor that the liquid is atomized. One end of the suction fiber mandrel 332 is contacted with the end face of the micro hole at the center position of the ultrasonic atomizing sheet 400. If the contact strength is too large, it will affect the vibration frequency of ultrasonic atomizing piece, or because of the large external force, the ultrasonic atomizing pieces is stopped working. In order to seek a kind of the most moderate range of activities intensity, so a spring with characteristic flexibility is selected as the support of the force. And this product is different from the general household ultrasonic atomizer in work environment. The household atomizer is placed on the table or on the ground, so that the end face of the suction fiber mandrel and the end face of the central micro hole of the ultrasonic atomizing piece can last forever once the suitable position is found. But this product is a kind of portable atomization device for human body, it moves following the human body, sometimes even intense exercises following the human body, at this time, if there is no retractable spring as the support of the movable range, the ultrasonic atomizing film is difficult to keep in the best working condition.

It is known to all that there is a medical instrument for the treatment of respiratory diseases in the ear, nose and throat specialist in the hospital. The interior of the instrument is provided with a liquid container with a special shape, the liquid container is provided with an ultrasonic atomizing head with a high vibration rate (not ultrasonic atomizing piece), the atomizing head is submerged in the drug liquid atomizing the drug liquid in the container. The liquid is constantly atomized into a fog of medicinal nature emerging the surface of the drug liquid. Furtherly, the fog with medicinal properties is stored in the space of the containers. Then, the electric fan set in the instrument sucks the outside air into it through a air filter, then enters the ventilation pipe connected to the liquid container into the liquid container to produce pressure.

The principle that the pressure produced in the liquid container is driven, the mist with medicinal ingredients stored in the space of the liquid container is squeezed out another pipe that is in contact with the patient's mouth by pressure, subsequently, the mist with medicinal ingredients enters the mouth of the patient and goes straight to the respiratory tract and plays a role in the treatment of respiratory diseases. Thus it can be seen that the drug will not destroy its composition and influence its efficacy during the atomization of drugs.

It shall be understood, the ultrasonic atomizing piece used in the invention can atomize the liquid water and produce water mist, but it can not change the molecule structure of the water, and it can not change the molecular structure of other substances dissolved in water. The user adds other water-soluble substances to the water in the water tank 300 as needed, for example essence, essential oils, or drugs etc. In the atomization process essence, essential oils or drugs is alasp atomized without destroying its ingredient, or changing their molecular structure. Therefore, the portable pneumatic atomizing device in the invention is not limited to use for cooling body, it can also be daily used or as the atomization of medical equipment.

Furthermore, the portable pneumatic atomizing device in the invention has characteristics of a portable wearable products, it can be worn and hand held. Therefore, the portable pneumatic atomizing device in the invention can be used for treatment of part patient on human body, especially convenient and effective for the treatment of various skin diseases.

The most common medical treatment for skin diseases is the application of creams on the surface of the skin. The creams is fused directly with the sweat on the body surface, that will destroy efficacy of drug and pesticide effect. Further, the creams is contaminated with the user's clothes. If the drug in the range of the acceptable viscosity of the atomizing capacity of the ultrasonic atomizing piece is added to the water tank of the portable pneumatic atomizing device of the invention, the drug can be atomized with air flow into the pores of the skin, it can make agents maximize its potency.

For example, the perfume or the essential oil is mixed into the water in the water tank 300, the portable pneumatic atomizing device can be used for indoor fragrance.

Preferably, the fan assemble 200 also comprises a belt buckle 240. In one embodiment of the present invention, the belt fastener 240 has a pair, disposed on both sides of the housing 210 and buckled on the man's belt. It is easy to carry. The water tank is also provided with a fixing clamp. The fixing clamp aids the belt buckle 240 to fix the portable pneumatic atomizing device on the belt.

Preferably, the shell 210 is provided with an ultrasonic atomizer plate switch and the switch of the fan 250.

Preferably, the side of the base is arranged with a power supply interface 131, when the power of the device runs out, the external power is used to supply power for the device, such as portable battery.

Preferably, the portable pneumatic atomizing device is also provided with a Bluetooth communication device, and it can be real-time docking with mobile device, thus it can freely control all the action of the cooling equipment, and it can directly observe all of the working state of the equipment in the mobile device.

The above is a further detailed description of the present invention in combination with a specific preferred embodiment, the specific implementation of the present invention cannot be limited to these instructions. For the general technical personnel in the technical field of the invention, without departing from the basic conception of the invention, its structure can be flexible and changeable and derive a series of products. If it just makes some simple deduction or replacement, it shall be deemed to belong to the scope of patent protection determined by the claims submitted by the invention.

What is claimed is:

1. A portable pneumatic atomizing device, wherein including a mounting seat, a small-type fan, a water tank, a ultrasonic atomizing piece and a fixing clip; said small-type fan and said water tank are respectively installed on an upper part and a side part of said mounting seat, and an air passage is formed among said small type fan, said water tank and said mounting seat; said mounting seat is provided with a lifting support frame, said lifting support frame adapted to stretch clothes to extend a gap between said clothes and human body; said ultrasonic atomizing piece is arranged on the top of said water tank and atomizes water in said water tank adapted to release into said gap between said clothes and said human body; said small type fan transfers outside air into said air passage, then capable of passing said air passage, into said gap between said clothes and said human body; a included angle between directions that said air and said water mist are adapted to enter into said gap between said clothes and said human body is beta angle, $0<\beta\leq 45°$.

2. The portable pneumatic atomizing device according to claim 1, wherein said mounting seat has a base, two sides of said base are respectively extended out of one arm; said water tank is arranged at said upper end of the base and is positioned between two said arms.

3. The portable pneumatic atomizing device according to claim 2, wherein said small type fan includes a shell, a fan assembly and a power assembly; said shell, said arms, said water tank and said base are combined to form said air passage; said shell has an air diversion portion and a fan portion; said air diversion portion is mounted on said arms and said base in a direction substantially parallel to said base and said water tank; the lower part of said air diversion portion protrudes downwards and outwards in a linear shape to form said fan portion; said included angle between the directions of said fan portion and said air diversion portion are set as alpha angle, $90<\alpha<180°$, so as to said included angle between the direction of air entering the air passage and out flowing of the air passage is alpha angle; said fan assembly is accommodated in said fan portion.

4. The portable pneumatic atomizing device according to claim 3, wherein said fan portion is provide with a safety net cover.

5. The portable pneumatic atomizing device according to claim 1, wherein said support frame is provided with a support plate, both ends of said supporting plate respectively extends a connecting piece, said connecting piece extends downwards to form a elongated slider, the centre of said slider is hollowed out into a slide slot; on the upper part of both sides of said water tank is respectively provided with a limiting piece, said limiting piece passes through the slide slot to slide mount the support frame on the water tank, and limits the lifting distance of said sliding piece.

6. The portable pneumatic atomizing device according to claim 5, wherein one side of said slider is attached to one side of said arm, the other side of said slider is a jagged edge; the two sides of said water tank is also respectively provided with an teeth block, wherein said teeth block is meshed with said jagged edge.

7. The portable pneumatic atomizing device according to claim 1, wherein said clothes fixing clamp is arranged at said upper part of said small type fan; said clothes fixing clamp is an elastic piece in W shape, M shape, U shape, O shape, V shape, N shape or T shape.

8. The portable pneumatic atomizing device according to claim 1, wherein said water tank comprises a box body, a box cover and a suction fiber mandrel tube; said box cover is buckled on said box body; an opening is arranged on said box cover, and water is poured into said box body through said opening; said box cover is provided with an installation groove, said installation groove is provided with said ultrasonic atomizing piece; said suction fiber mandrel tube is aslant arranged in said box body; a suction fiber mandrel and a spring are arranged in the suction fiber mandrel tube, and said spring is arranged between the bottom end surface of said suction fiber mandrel and the sealing surface at said bottom of said suction fiber mandrel tube.

9. The portable pneumatic atomizing device according to claim 8, wherein the side surface of said lower end of said suction fiber mandrel tube is provided with an inlet; said water in said water tank enters said suction fiber mandrel tube by said inlet to moist said suction fiber mandrel.

10. The portable pneumatic atomizing device according to claim 2, wherein both sides of said water tank are arranged a belt fixed buckle.

* * * * *